United States Patent [19]

Bullard, Jr.

[11] Patent Number: 4,923,453
[45] Date of Patent: May 8, 1990

[54] ABSORBENT DISPOSABLE COVER

[76] Inventor: Milton Bullard, Jr., 3766 31th St. #7, San Diego, Calif. 92104

[21] Appl. No.: 300,318

[22] Filed: Jan. 23, 1989

[51] Int. Cl.$^5$ .............................................. A61F 13/10
[52] U.S. Cl. .................................... 604/356; 604/322; 128/855; 5/484
[58] Field of Search ............... 604/354, 322, 317, 358, 604/385.1, 356, 359; 5/484, 500, 90, 507, 496, 497, 502, 487; 128/849, 855

[56] References Cited

U.S. PATENT DOCUMENTS

| | | | |
|---|---|---|---|
| 3,407,414 | 4/1968 | Burns et al. | 5/335 |
| 3,427,670 | 2/1969 | Mimoy | 5/484 |
| 3,528,421 | 9/1970 | Vaillancourt et al. | 604/372 |
| 3,576,039 | 4/1971 | Roberts | 5/484 X |
| 3,646,624 | 5/1972 | Zipf | 5/334 |
| 3,670,345 | 9/1972 | Poll et al. | 5/91 |
| 3,763,907 | 10/1973 | Hockley et al. | 5/484 X |
| 3,958,286 | 7/1976 | Rodinsky | 5/335 |
| 4,363,322 | 12/1982 | Andersson | 604/359 |
| 4,547,195 | 10/1985 | Jackson | 604/359 |
| 4,664,959 | 10/1987 | Dagenais | 428/74 |

FOREIGN PATENT DOCUMENTS 403237 9/1909 France .................................... 5/484

Primary Examiner—Richard J. Apley
Assistant Examiner—Rachel M. Healey
Attorney, Agent, or Firm—Andsel Group

[57] ABSTRACT

An absorbent disposable cover for hospital X-ray tables and the like. The cover has a bottom layer in the form of a sheet of plastic material that is impermeable to moisture, an intermediate fluid absorbent layer that functions as a blotter that will absorb and disperse any fluid it comes in contact with, and a top layer in the form of a sheet of material of semi-permeable material that will permit the flow of fluids into the intermediate fluid absorbent layer. A pre-formed corner pocket is formed at the respective corners of the cover and adhesive pads are attached to their bottom surface for detachably securing them to the corners of a table upon which the absorbent disposable cover has been placed. The covers are folded into a compact rectangular shape and stacked in a carton having a cutout slot in its top wall. The cover has been folded in such a manner that the pre-formed cover pockets are on top and located in the area of the cutout slots so they can be grasp for pulling the cover out of the dispensing slot.

5 Claims, 1 Drawing Sheet

U.S. Patent  May 8, 1990  4,923,453
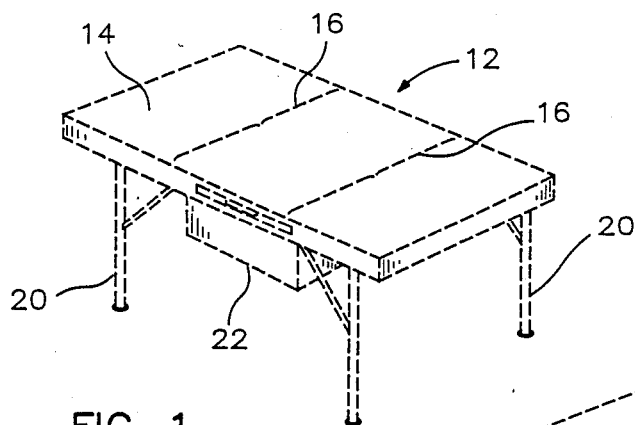
FIG. 1
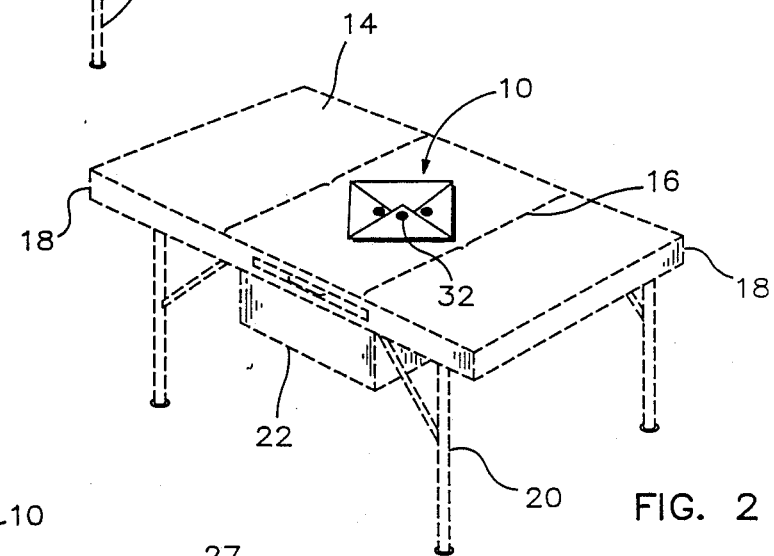
FIG. 2
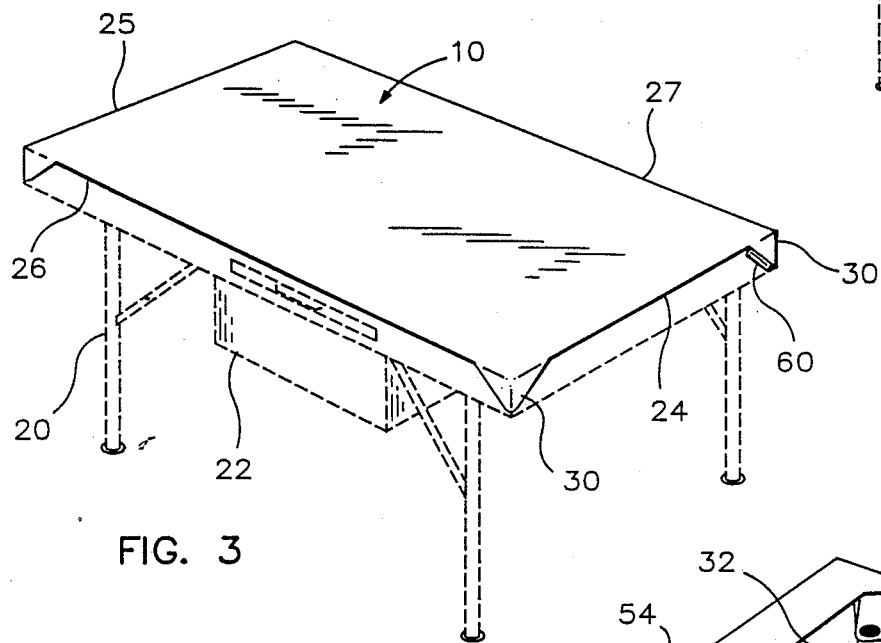
FIG. 3
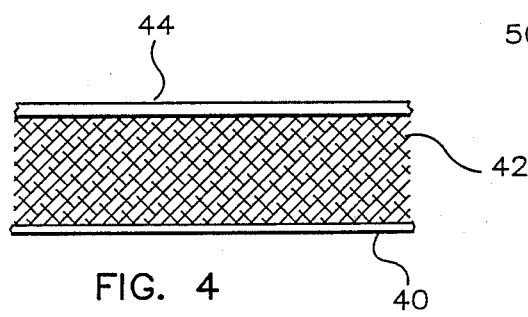
FIG. 4
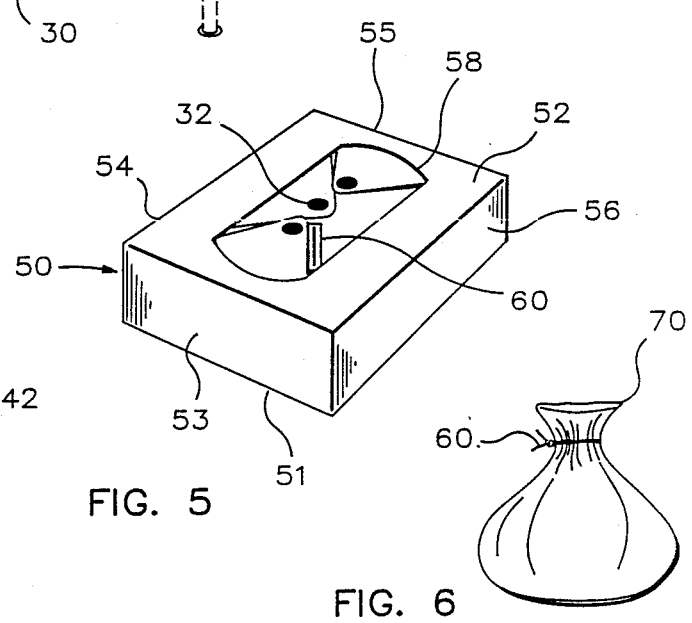
FIG. 5
FIG. 6

ABSORBENT DISPOSABLE COVER

BACKGROUND OF THE INVENTION

The invention relates to a cover and more specifically to an absorbent disposable cover for hospital X-ray tables and the like.

Hospitals and clinics are faced with rising costs. Labor and equipment time represent a significant portion of the costs.

Each day thousands of patients have barium enema X-ray examinations. Quite frequently the patient is unable to hold the enema fluid and an embarrassing accident occurs which contaminates the X-ray table. X-ray tables are usually vinyl and have the X-ray film tray located under the table surface. When the aforementioned accidents occur the fluid will cover the table surface and can seep down into the film tray. The fluid contaminates the area and also obscures the area that must be X-rayed so the area must be cleaned before the proceedure can be finished. Electrical shorts due to the liquid could be a potential problem. Also a prime factor is the time lost to the cleaning up of the patient and table area before crucial X-rays can be taken.

In addition to X-ray tables, hospitals also have trauma centers with examination tables. These tables can be contaminated with blood, urine and fecal material. Again, cleanup prior to the next use is lengthy and expensive. Ambulances have gurneys and the surface must be changed after each use.

Some hospitals use cloth sheeting to cover the tables. The sheeting must be laundered and is expensive to replace. Costs involved are the sheets, laundry facility maintenance, and time consumed to change the sheets. Where sheeting is not used, vinyl covered table surfaces are used. Vinyl needs to wiped down with disinfectant after each use.

A further area requiring attention is when X-ray patients move to a restroom after having an accident on the X-ray table. If the patient loses enema fluid as they go to the restroom the floor also becomes contaminated requiring manpower and time for the clean-up.

The invention provides a simple to use, inexpensive and simple solution to the above listed problems. A disposable table surface, impermeable to fluids, with an absorbent center blotter which is covered with a semi-permeable upper contact sheet will solve the problems listed above. Any fluid, blood, urine or enema will be absorbed without soaking through to the table surface. Clean-up is simple, the four stick-down corners are lifted and folded to the center. By picking up the cover with the blotter inward and keeping the plastic sheet outward, the moisture is contained. The contaminated table cover can be easily disposed of and a replacement easily attached to the table.

The time it takes to clean an area is shortened when the disposable pad is used. It requires less clean up time for hospital or clinic personnel and the time that equipment, X-ray tables, gurneys, examination tables, etc. are out of service is shortened. Time savings and equipment turn-around time represent money and real costs to a hospital.

There is, therefore, a need for a disposable, cost effective X-ray table cover pad which can speed table use turn-around time and personnel labor expenditure.

SUMMARY OF THE INVENTION

Applicant's invention is an absorbent utility cover primarily for use in hospitals and clinics as a sacrifical surface for covering X-ray tables, emergency room tables, gurneys, and examination tables or cots.

The invention is a folded bed spread cover with pre-formed pocketed corners. The corners have adhesive pads to adhere to the vinyl of the table. The cover has three layers, a bottom layer of thin waterproof plastic, a central absorbent blotter of lightweight fiberous material treated with deodorant and antiseptic, and a top semi-porous layer, similar to childrens diaper liners.

The covers come packaged several to a carton where each unit is pre-folded in a four cornered fold with the corners up. To use, simply pick a cover from the carton and place the cover in the center of a table. Unfolding the cover puts each of the pocket pouches near a table corner. Each pocket pouch has an adhesive patch located thereon. By merely affixing the adhesive patch of the pocket pouch to the table corner the cover is properly deployed and spread smoothly over the table surface.

The purpose of the invention is to provide an absorbent, clean and disposable surface for each patient and a fast, cleanup for hospital and clinic personnel.

DESCRIPTION OF THE DRAWINGS

FIG. 1 is a front perspective view of an X-ray table;

FIG. 2 is a front perspective view of the X-ray table with the folded absorbent cover placed centrally thereon;

FIG. 3 is a front perspective view of an X-ray table with the absorbent disposable cover unfolded and secured in position;

FIG. 4 is a cross sectional view taken along circular line 4—4 of FIG. 3;

FIG. 5 is a front perspective view of a carton within which the folded absorbent disposable covers are dispensed; and FIG. 6 is a front perspective view illustrating the absorbent disposable cover after it has been used and gathered upwardly from its four corners to form a disposable bag type structure.

DESCRIPTION OF THE PREFERRED EMBODIMENT

Applicant's novel absorbent disposable cover for hospital X-ray tables and the like will now be described by referring to FIGS. 1-6 of the drawings. The absorbent disposable cover is generally designated numeral 10.

An X-ray table 12 is illustrated in FIGS. 1-3 and it has a top surface 14 having creases 16 therein. It has corners 18 and legs 20. An X-ray film tray 22 is mounted to the underside of the table.

Absorbent disposable cover 10 has a front edge 24, a rear edge 25, and laterally spaced side edges 26 and 27. Pre-formed corner pockets 30 are formed at its respective corners and they have adhesive pads 32 attached to their bottom surface. Preformed corner pockets 30 have a triangular configuration. A cross sectional view of the cover 10 is illustrated in FIG. 4. It shows a bottom layer 40 in the form of a sheet of plastic material that is impermeable to moisture. Intermediate layer 42 is a fluid absorbent layer that functions as a blotter that will absorb and disperse any fluid it comes into contact with. Top layer 44 is in the form of a sheet of material of semi-permeable material that will permit the flow of fluids into the intermediate fluid absorbent layer.

Absorbent disposable cover 10 is shown in FIG. 2 folded into a compact configuration with the bottom surface of preformed corner pockets 30 facing upwardly therefrom. This is the state in which the absorbent disposable cover is withdrawn from its carton 50. Carton 50 has a bottom wall 51, a top wall 52, and side walls 53, 54, 55, and 56. A cutout slot 58 is formed in top wall 52 and it allows access to the folded absorbent disposable covers 10. A tie wire 60 is secured to the edge of one of the pre-formed cover pockets 30.

In FIG. 6 the absorbent disposable cover is shown as it would appear after it has been removed from the X-ray table by means of taking the respective four corners and drawing them toward each other to form them in the shape of a bag 70. At this stage the absorbent disposable cover can easily be disposed of without spilling any of the contents.

The drawings as shown and thusly described represent the preferred embodiment of the invention. It would be obvious to one skilled in the art that various changes and modifications, simple or complex, could be made to the preferred embodiment that would alter the appearance but not the scope, spirit and intention of the invention. It is the intention of the inventor to preclude of occurrence of such emulations in scope or spirit through the following claims.

What is claimed is:

1. An absorbent disposable cover for hospital x-ray tables and the like comprising:

a rectangularly shaped cover having a bottom layer in the form of a sheet of plastic material that is impermeable to moisture, an intermediate fluid absorbent layer that functions as a blotter that will absorb and disperse any fluid that it comes in contact with, and a top layer in the form of a sheet of material of semi-permeable material that will permit the flow of fluids into said intermediate fluid absorbent layer;

said cover having corners formed by a front edge, a rear edge, and laterally spaced side edges, a pre-formed corner pocket at the respective corners, said corner pockets having a top surface and a bottom surface, adhesive pads are attached to the bottom surface of said pre-formed corner pockets for detachably securing them to the corners of a table upon which the absorbent disposable cover has been placed; and said rectangularly shaped cover being folded into a compact rectangular shape with the respective four pre-formed corner pockets having their bottom surfaces facing upwardly and being on top of said folded cover.

2. An absorbent disposable cover as recited in claim 1 in combination with an X-ray table and wherein said cover has been unfolded and the adhesive pads on the bottom surface of said preformed corner pockets have been adhered to the respective corners of said X-ray table.

3. An absorbent disposable cover as recited in claim 1 further comprising a carton having a top wall, a bottom wall, and side walls, a cutout slot being formed in said top wall and said folded covers are packaged in a stack within said carton with their pre-formed corner pockets located in the area of said cutout slot so that they can be grasped for pulling said cover out of said dispensing slot.

4. An absorbent disposable cover as recited in claim 1 wherein said intermediate fluid absorbent layer has been treated with a deoderant and a mild anti-septic.

5. An absorbent disposable cover as recited in claim 1 further comprising a tie wire secured to one of the corners of said cover.

* * * * *